United States Patent [19]

Yoon et al.

[11] Patent Number: 5,496,947
[45] Date of Patent: Mar. 5, 1996

[54] QUINOLONE CARBOXYLIC ACID DERIVATIVES

[75] Inventors: Sung-June Yoon, Seoul; Young-Ho Chung, Kyunggi-do; Chi-Woo Lee, Anyang; Yoon-Seok Oh, Kyungki-do; Dong-Rack Choi, Kyungki; Nam-Doo Kim, Kyungki, all of Rep. of Korea

[73] Assignee: Dong Wha Pharmaceutical Industrial Co., Ltd., Rep. of Korea

[21] Appl. No.: 193,475

[22] Filed: Feb. 8, 1994

[51] Int. Cl.$^6$ .................. C07D 471/04; C07D 401/14
[52] U.S. Cl. .................. 544/362; 544/363; 546/123; 546/156; 546/275; 546/312
[58] Field of Search ................... 546/156, 123; 544/362, 363; 514/300, 312, 254

[56] References Cited

U.S. PATENT DOCUMENTS

| | | | |
|---|---|---|---|
| 4,146,719 | 3/1979 | Irikura | 544/363 |
| 4,556,658 | 12/1985 | Grohe et al. | 514/254 |
| 4,617,308 | 10/1986 | Mich et al. | 514/312 |
| 4,620,007 | 10/1986 | Grohe et al. | 546/156 |
| 4,670,444 | 6/1987 | Grohe et al. | 514/300 |
| 4,704,459 | 11/1987 | Todo et al. | 546/123 |

FOREIGN PATENT DOCUMENTS

| | | |
|---|---|---|
| 131839 | 1/1985 | European Pat. Off. . |
| 61-152682 | 7/1986 | Japan . |
| 61-251667 | 8/1986 | Japan . |
| 62-174053 | 7/1987 | Japan . |
| 2-85255 | 3/1990 | Japan . |

OTHER PUBLICATIONS

Miyamoto et al., *Chemical Abstracts*, vol. 106, No. 119709 (Abstract for JP61–251667, Nov. 8, 1986) (1987).
Narita et al., *Chemical Abstracts*, vol. 106, No. 213923 (Abstract for JP62 33176, Feb. 13, 1987) (1987).
Matsumoto et al., *Chemical Abstracts*, vol. 107, No. 39861 (Abstract for JP61 152682, Jul. 11, 1986) (1987).
Jacquet et al., *Heterocycles*, vol. 34, p. 2301 (1992).
Talik et al., Ann. Soc. Chim. Polonorum, vol. 38, pp. 777–783 (1964).
Chu et al., J. Med. Chem., vol. 34, pp. 168–174 (1991).
Chu et al., J. Med. Chem., vol. 29, pp. 2363–2369 (1986).
Hand et al., "Syntheses of 2–Chloro– and 2–Amino–5–fluoropyridines and Isolation of a Novel Difluoroboryl Imidate", pp. 905–908 (1989).
Abstract of JP 2–85255, Chem. Abstr., vol. 113, pp. 636 (1990), Narita et al.
Chem. Abstr. 107, No. 39864 (1987), Izquierdo et al.

*Primary Examiner*—Emily Bernhardt
*Attorney, Agent, or Firm*—Birch, Stewart, Kolasch & Birch

[57] ABSTRACT

The present invention relates to the novel quinolone carboxylic acid derivatives of the following formula (I) and their pharmaceutically acceptable salts and their hydrates.

wherein
X is a hydrocarbon, fluorocarbon or nitrogen atom,
Y is a hydrogen or methyl group,
$R^1$ is a hydrogen or alkyl group having 1 to 5 carbon atom,
$R^2$ is wherein A and B is a fluorocarbon or nitrogen atom, provided that, if A=CF, B=N and if A=N, B=CF) and
$R^3$ is (wherein $R^4$ is an amino group which makes a racemate or (S)-enantiomer) or (wherein $R^5$, $R^6$ and $R^7$ are respectively hydrogen or alkyl group having 1 to 3 carbon atom.).

The compounds according to the present invention are used as antibacterial agents.

2 Claims, No Drawings

QUINOLONE CARBOXYLIC ACID DERIVATIVES

BACKGROUND OF THE INVENTION

The present invention relates to the novel quinolone carboxylic acid derivatives, their esters, their pharmaceutically acceptable salts and their hydrates as shown in formula (I) and a process for preparing these compounds. Furthermore, some of the invented quinolone carboxylic acid derivatives as shown in formula (I) show broad spectrum and excellent pharmacokinetic properties and low toxicity.

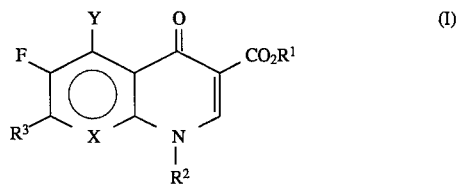

wherein

X is a hydrocarbon, fluorocarbon or nitrogen atom,

Y is a hydrogen or methyl group, $R^1$ is a hydrogen or $C_1$–$C_5$ alkyl group, $R^2$ is

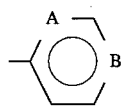

(wherein A and B are fluorocarbon or nitrogen atom, provided that if A=CF, B=N and if A=N, B=CF)

$R^3$ is

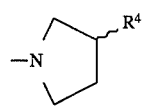

(wherein $R^4$ is an amino group to make a racemate or (S)-enantiomer.) or

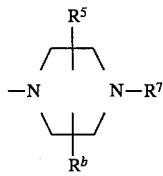

(wherein $R^5$, $R^6$ and $R^7$ are H— or $C_1$–$C_3$ alkyl groups.)

In general, most of the quinolone-type antibiotics which have been heretofore developed are ones having small alkyl and cycloalkyl group at N-1 position [e.g. Norfloxacin: U.S. Pat. No. 4,146,719, Ciprofloxacin: [U.S. Pat. No. 4,620,007] and ones having aromatic group at N-1 position [e.g. Temafloxacin: J. Med. Chem., 34, 168 (1991), Tosufloxacin: U.S. Pat. No. 4,704,459].

However, a noticeable quinolone antibiotic having heteroaromatic group at N-1 position has not been yet developed. Otsuka, Toyama and others reported their researches upon introducing heteroaromatic group such as furyl, thienyl, thiazol, imidazol, pyridyl, pyrimidyl group at N-I position, but a compound available in vivo has not been yet developed. (JPK 61-251667-A, 62-174053-A, 02-85255-A).

In particular, the compounds developed up to now generally have good in vitro activity, but such in vitro activity could not leads to in vivo because of poor pharmacokinetics including half-life ($t_{1/2}$), maximum blood level ($C_{max}$), bioavilability (BA), area under curve (AUC) etc, which are important properties of a compound for good in vitro activity to be maintained in vivo.

Therefore, the object of this invention is to develope compounds having excellent pharmacokinetic properties by introducing fluoro pyridyl group which is a heteroaromatic group at N-1 position, thereby to produce compounds having good antibiotic power in vivo and long half-life ($t_{1/2}$) which enable once a day of dose. Therefore, the present invention provides a series of compounds having even more excellent pharmacokinetic properties than those of the conventional quinolone antibiotics by introducing 5-fluoro-2-pyridyl group and 3-fluoro-4-pyridyl group into mother nuclei of quinolone and naphthyridine.

SUMMARY OF THE INVENTION

The present invention relates to novel quinolone carboxylic acid derivatives which have a fluoropyridine group at N-1 position.

The object of the present invention is to provide the novel quinolone carboxylic acids, their esters, their pharmaceutically acceptable salts, and their hydrates in which are some compounds having broad spectrums, excellent pharmacokinetic properties and low toxicity which are important factors for a drug to be administered and function in the body, and a process for preparing these compounds.

Some of these quinolone derivatives have longer half-life ($t_{1/2}$), even higher maximum blood level ($C_{max}$) and bioavailability (BA) and even larger area under curve (AUC) compared to ciprofloxacin of the prior art. In addition, they have still far longer half-life ($t_{1/2}$) and larger area under curve (AUC) compared to ofloxacin which is known to have excellent pharmacokinetics. Accordingly, some of the novel quinolone carboxylic acid derivatives of the present invention are expected to have highly increased in vivo activity.

DETAILED DESCRIPTION OF THE INVENTION

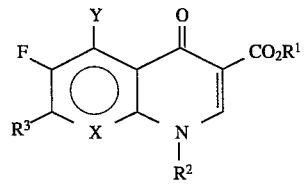

wherein

X is a hydrocarbon, fluorocarbon or nitrogen atom,

Y is a hydrogen or methyl group, $R^1$ is a hydrogen or $C_1$–$C_5$ group, $R^2$ is

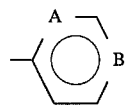

wherein A and B are fluorocarbon or nitrogen atom, provided that if A=CF, B=N and if A=N, B=CF)

$R^3$ is

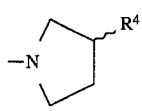

(wherein $R^4$ is an amino group to make a racemate or (S)-enantiomer.) or $R^3$ is

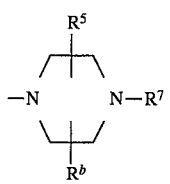

(wherein $R^5$, $R^6$ and $R^7$ are H— or $C_1$–$C_3$ alkyl groups.)

The compound of the formula (I) can be prepared as follows. Each compound in the formula (I) is prepared by the substantially same method except the reaction temperature, irrespective of the kind of X, Y, Z in the compound of the formula (II).

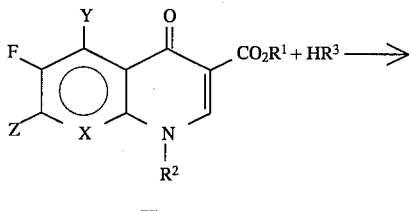

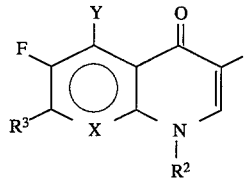

(I)

wherein X, Y, Z, $R^1$, $R^2$ and $R^3$ are each as described above.

The above reaction is carried out in a solvent selected from the alcohols such as methanol, ethanol, the ethers such as tetrahydrofuran, dioxane, 1,2-dimethoxyethane, diglyme, aromatic hydrocarbons such as benzene, toluene, xylene, and the inert solvents such as acetonitrile, N,N-dimethylformamide, dimethyl sulfoxide, pyridine etc., at 0° C. to 150° C. temperature for 5 minutes to 48 hours. In addition, the above reaction is generally carried out in the presence of an acid-acceptor, the desirable amount of which is 1 to 3 equivalent of the compound (II). Alternatively, an excess of the compound (VI) may be used as an acid-acceptor. As an acid-acceptor, a tertiary amine such as pyridine, triethylamine or 1,8-diazabicyclo[5.4.0]undec-7-ene, or an alkali metal carbonate such as sodium hydrogen carbonate, sodium carbonate or potassium carbonate may be used.

In order to prepare the compound of the formula (I) wherein $R^1$ is a hydrogen, the compound of the formula (II") (wherein $R^1$ is a hydrogen) and $HR^3$ of the formula (VI) (wherein $R^3$ is the same as described above) can be reacted; or otherwise the compound of the formula (II') (wherein $R^1$ is an alkyl group) and $HR^3$ of the formula (VI) (wherein $R^3$ is the same as described above) can be reacted first and then hydrolysis using an acid or alkali can be carried out. At this time, in the acidic hydrolysis may be used an acid such as hydrochloric acid and sulfuric acid and in the alkaline hydrolysis may be used an alkali such as sodium hydroxide and potassium hydroxide. The acid or alkali may be used in the hydrolysis as a solution in water or water-containing ethanol or methanol.

The compound of the formula (II) can be prepared as follows. (II=II'+II")

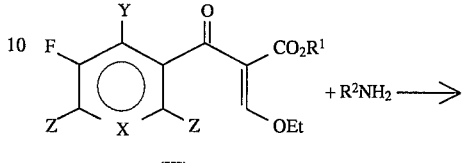

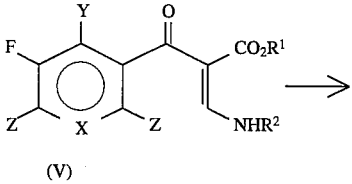

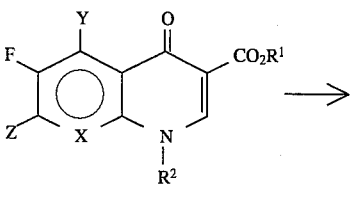

(II')

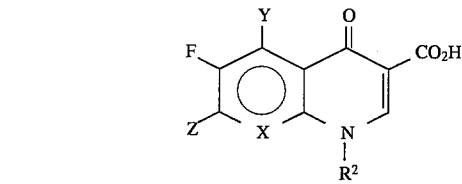

(II")

wherein X, Y, Z, $R^1$ and $R^2$ are each as defined above.

The compound of the formula (III) is prepared by the conventional method [Ger. Offen. DE 3,142,854; Ger. Offen. DE 3,318,145; J. Med. Chem., 29, 2363(1986)] and thereby obtained compound of the formula (III) is reacted with the compound of the formula (IV) prepared by the conventional method [Rocz. chem., 777–783(1964); Synthesis, 12, 905–908(1989)] in an alcohol solvent such as methanol and ethanol, or a haloformic solvent such as dichloromethane and chloroform at −10° C.− 30° C. to obtain the compound of the formula (V). The obtained compound of the formula (V) is subjected to a ring-closing reaction using potassium carbonate and 18-crown-6 in acetonitrile, or a ring-closing reaction using sodium hydride in N,N-dimethyl formamide, to obtain the compound of the formula (II'). At this time the reaction temperature is desirably from 0° C. to the reflux temperature. The compound of the formula (II') is hydrolyzed by treatment with an acid or alkali to obtain the compound of the formula (II') and the compounds of the formula (II') and (II") are designated totally as the formula (II). At this time, in the acidic hydrolysis may be used an acid such as hydrochloric acid or sulfuric acid, and in the alkaline hydrolysis may he used an alkali such as sodium hydroxide or potassium hydroxide. The acid or alkali may he used in the hydrolysis as a solution in water or water-containing ethanol or methanol.

Representative examples of the novel quinolone carboxylic acid derivatives according to the present invention are as follows;

1. 1-(3-fluoro-4-pyridyl)-6-fluoro-7-(1-piperazinyl)-1,4-dihydro-4-oxoquinoline-3-carboxylic acid
2. 1-(3-fluoro-4-pyridyl)-6-fluoro-7-(4-methyl-1-piperazinyl)-1,4-dihydro-4-oxoquinoline-3-carboxylic acid
3. 1-(3-fluoro-4-pyridyl)-6-fluoro-7-(3-methyl-1-piperazinyl)-1,4-dihydro-4-oxoquinoline-3-carboxylic acid
4. 1-(3-fluoro-4-pyridyl)-6-fluoro-7-(3,5-dimethyl-1-piperazinyl)-1,4-dihydro-4-oxoquinoline-3-carboxylic acid
5. 1-(3-fluoro-4-pyridyl)-6-fluoro-7-(3-amino-1-pyrrolidinyl)-1,4-dihydro-4-oxoquinoline-3-carboxylic acid
6. 1-(3-fluoro-4-pyridyl)-6-fluoro-7-[(3S)-3-amino-1-pyrrolidinyl]-1,4-dihydro-4-oxoquinoline-3-carboxylic acid
7. 1-(3-fluoro-4-pyridyl)-6-fluoro-7-(1-piperazinyl)-1,4-dihydro-4-oxo-1,8-naphthyridine-3-carboxylic acid
8. 1-(3-fluoro-4-pyridyl)-6-fluoro-7-(4-methyl-1-piperazinyl)-1,4-dihydro-4-naphthyridine-3-carboxylic acid
9. 1-(3-fluoro-4-pyridyl)-6-fluoro-7-(3-methyl-1-piperazinyl)-1,4-dihydro-4-oxo-1,8-naphthyridine-3-carboxylic acid
10. 1-(3-fluoro-4-pyridyl)-6-fluoro-7-(3,5-dimethyl-1-piperazinyl)-1,4-dihydro-4-oxo-1,8-naphthyridine-3-carboxylic acid
11. 1-(3-fluoro-4-pyridyl)-6-fluoro-7-[(3S)-3-amino-1-pyrrolidinyl)-1,4-dihydro-4-oxo-1,8-naphthyridine-3-carboxylic acid
12. 1-(5-fluoro-2-pyridyl)-6-fluoro-7-(1-piperazinyl)-1,4-dihydro-4-oxo-1,8-naphthyridine-3-carboxylic acid
13. 1-(5-fluoro-2-pyridyl)-6-fluoro-7-(4-methyl-1-piperazinyl)-1,4-dihydro-4-oxo-1,8-naphthyridine-3-carboxylic acid
14. 1-(5-fluoro-2-pyridyl)-6-fluoro-7-(3-methyl-1-piperazinyl)-1,4-dihydro-4-oxo-1,8-naphthyridine-3-carboxylic acid
15. 1-(5-fluoro-2-pyridyl)-6-fluoro-7-(3,5-dimethyl-1-piperazinyl)-1,4-dihydro-4-oxo-1,8-naphthyridine-3-carboxylic acid
16. 1-(5-fluoro-2-pyridyl)-6-fluoro-7-(3-amino-1-pyrrolidinyl)-1,4-dihydro-4-oxo-1,8-naphthyridine-3-carboxylic acid
17. 1-(5-fluoro-2-pyridyl)-6-fluoro-7-(1-piperazinyl)-1,4-dihydro-4-oxoquinoline-3-carboxylic acid
18. 1-(5-fluoro-2-pyridyl)-6-fluoro-7-(4-methyl-1-piperazinyl)-1,4-dihydro-4-oxoquinoline-3-carboxylic acid
19. 1-(5-fluoro-2-pyridyl)-6-fluoro-7-(3-methyl-1-piperazinyl)-1,4-dihydro-4-oxoquinoline-3-carboxylic acid
20. 1-(5-fluoro-2-pyridyl)-6-fluoro-7-(3,5-dimethyl-1-piperazinyl)-1,4-dihydro-4-oxoquinoline-3-carboxylic acid
21. 1-(5-fluoro-2-pyridyl)-6-fluoro-7-(3-amino-1-pyrrolidinyl)-1,4-dihydro-4-oxoquinoline-3-carboxylic acid
22. 1-(5-fluoro-2-pyridyl)-6-fluoro-7-[(3S)-3-amino-1-pyrrolidinyl)-1,4-dihydro-4-oxoquinoline-3-carboxylic acid
23. 1-(5-fluoro-2-pyridyl)-6,8-difluoro-7-(1-piperazinyl)-1,4-dihydro-4-oxoquinoline-3-carboxylic acid
24. 1-(5-fluoro-2-pyridyl)-6,8-difluoro-7-(4-methyl-1-piperazinyl)-1,4-dihydro-4-oxoquinoline-3-carboxylic acid
25. 1-(5-fluoro-2-pyridyl)-6,8-difluoro-7-(3-methyl-1-piperazinyl)-1,4-dihydro-4-oxoquinoline-3-carboxylic acid
26. 1-(5-fluoro-2-pyridyl)-6,8-difluoro-7-(3,5-dimethyl-1-piperazinyl)-1,4-dihydro-4-oxoquinoline-3-carboxylic acid
27. 1-(5-fluoro-2-pyridyl)-6,8-difluoro-7-(3-amino-1-pyrrolidinyl)-1,4-dihydro-4-oxoquinoline-3-carboxylic acid
28. 5-methyl-7-(4-methyl-1-piperazinyl)-1-(5-fluoro-2-pyridyl)-6-fluoro-1,4-dihydro-4-oxoquinoline-3-carboxylic acid
29. 5-methyl-7-(3-methyl-1-piperazinyl)-1-(5-fluoro-2-pyridyl)-6-fluoro-1,4-dihydro-4-oxoquinoline-3-carboxylic acid Meanwhile, the novel quinolone carboxylic acid derivatives according to this invention may be used as free compounds, acid addition salts thereof or salts of the carboxyl groups thereof. The suitable acids for salt formation include inorganic acids such as hydrochloric acid, phosphoric acid and organic acids such as acetic acid, oxalic acid, succinic acid, methanesulfonic acid, maleic acid, malonic acid, gluconic acid.

Pharmaceutically acceptable base salts of the above described compounds of the formula (I) are formed with alkali metals such as sodium, potassium or alkaline earth metals such as magnesium, calcium. The free compounds of the present invention, their acid addition salts and their salts of the carboxyl groups of pyridone carboxylic acid derivatives may exist as hydrates.

The following examples are provided to illustrate the desirable preparation of the compounds of the present invention.

Preparation 1

Preparation of ethyl 3-(3-fluoro-4-pyridyl)amino-2-(2,4,5-trifluorobenzoyl)acrylate 2.5 g of ethyl 2,4,5-trifluorobenzoyl acetate, 2.55 ml of triethyl o-formate, 12 ml of acetic anhydride are mixed together and refluxed for 3 to 5 hours, cooled to room temperature, and distilled under a reduced pressure. The obtained product is dissolved in 50 ml of anhydrous dichloromethane and added with 1.26 g of 4-amino-3-fluoropyridine and stirred at room temperature for 5 hours, and then concentrated under a reduced pressure. The product is used in the next reaction without further purification.

Preparation 2

Preparation of ethyl 3-(3-fluoro-4-pyridyl)amino-2-(2,6-dichloro-5-fluoronicotinyl) acrylate A procedure substantially similar to the procedure in Preparation 1 is carried out to prepare the title compound.

Preparation 3

Preparation of ethyl 3-(5-fluoro-2-pyridyl)amino-2-(2,6-dichloro-5-fluoronicotinyl) acrylate A procedure substantially similar to the procedure in Preparation 1 is carried out to prepare the title compound.

Preparation 4

Preparation of ethyl 3-(5-fluoro-2-pyridyl)amino-2-(2,3,4,5-tetrafluorobenzoyl) acrylate A procedure substantially similar to the procedure in Preparation 1 is carried out to prepare the title compound.

Preparation 5

Preparation of ethyl 3-(5-fluoro-2-pyridyl)amino-2-(2,4,5-trifluorobenzoyl)acrylate A procedure substantially similar to the procedure in Preparation 1 is carried out to prepare the title compound.

Preparation 6

Preparation of ethyl 3-(5-fluoro-2-pyridyl)amino-2-(3-methyl-2,4,5-trifluorobenzoyl)acrylate A procedure substantially similar to the procedure in Preparation 1 is carried out to prepare the title compound.

Preparation 7

Preparation of ethyl 1-(3-fluoro-4-pyridyl)-6,7-difluoro-1,4-dihydro-4-oxoquinoline-3-carboxylate 2.0 g of ethyl 3-(3-fluoro-4-pyridyl)amino-2-(2,4,5-trifluorobenzoyl)acrylate, 1.50 g of potassium carbonate and 0.43 g of 18-crown-6 are mixed with 40 ml of anhydrous acetonitrile.

The mixture is refluxed for 3 hours and then cooled, added with 100 ml of water and stirred during 30 minutes, then filtered and dried to obtain 1.3 g of the desired compound.

m.p.: 212° C.

$^1$H-NMR (CDCl$_3$, ppm): 1.26 (t,3H, J=7.20 Hz), 4.40(q, 2H, J=7.20 Hz), 6.50– 6.80 (m, 1H), 7.40–7.60(m, 1H), 8.22–8.42(m, 2H), 8.68–8.96(m, 2H)

Preparation 8

Preparation of ethyl 1-(3-fluoro-4-pyridyl)-6-fluoro-7-chloro-1,4-dihydro-4-oxo-1,8-naphthyridine-3-carboxylate A procedure substantially similar to the procedure in Preparation 7 is carried out to prepare the title compound.

m.p.: 226° C.

$^1$H-NMR (CDCl$_3$, ppm): 1.42(t, 3H, J=7.20 Hz), 4.42(q, 2H, J=7.20 Hz), 7.46– 7.50(m, 1H), 8.48–8.54(m, 2H), 8.70–8.82(m, 2H)

Preparation 9

Preparation of ethyl 1-(5-fluoro-2-pyridyl)-6-fluoro-7-chloro-1,4-dihydro-4-oxo-1,8-naphthyridine-3-carboxylate A procedure substantially similar to the procedure in Preparation 7 is carried out to prepare the title compound.

m.p.: 230° C.

$^1$H-NMR (CDCl$_3$, ppm): 1.36 (t, 3H, J=7.20 Hz), 4.38(q, 2H, J=7.20 Hz), 7.60– 7.80(m, 2H), 8.36–8.54(m,2H), 8.94(s, 1H)

Preparation 10

Preparation of ethyl 1-(5-fluoro-2-pyridyl)-6,7-difluoro-1,4-dihydro-4-oxoquinoline-3-carboxylate A procedure substantially similar to the procedure in Preparation 7 is carried out to prepare the title compound.

m.p.: 210°–213° C.

$^1$H-NMR (CDCl$_3$, ppm): 1.50(t, 3H, J=8.00 Hz), 4.70(q, 2H, J=8.00 Hz), 7.42(dd, 1H, J=3.04 Hz, J=10.04 Hz), 7.92–8.19(m, 2H), 8.50–8.79(m, 2H), 9.45(s, 1H)

Preparation 11

Preparation of ethyl 1-(5-fluoro-2-pyridyl)-6,7,8-trifluoro-1,4-dihydro-4oxoquinoline-3-carboxylate A procedure substantially similar to the procedure in Preparation 7 is carried out to prepare the title compound.

m.p.: 203°–205° C.

$^1$H-NMR (CDCl$_3$, ppm): 1.32(t, 3H, J=7.20 Hz), 4.32(q, 2H, J=7.20 Hz), 7.36– 7.72(m, 2), 8.00–8.22(m, 1H), 8.30–8.50(m, 2H)

Preparation 12

Preparation of 1-(3-fluoro-4-pyridyl)-6,7-difluoro-1,4-dihydro-4-oxoquinoline-3-carboxylic acid 5 g of ethyl 1-(3-fluoro-4-pyridyl)-6,7-difluoro-1,4-dihydro-4-oxoquinoline-3-carboxylate is added with 20 ml of water, 30 ml of ethanol and 15 ml of conc. hydrochloric acid and refluxed for 8 hours. After cooling to room temperature and standing for 2 hours, filtering and drying are carried out to obtain 4.2 g of the desired compound.

m.p.: 271°–273° C.

$^1$H-NMR (CF$_3$COOD, ppm): 7.28–7.58(m, 1H), 8.26–8.88(m, 2H), 9.22–9.62(m, 3H)

Preparation 13

Preparation of 1-(3-fluoro-4-pyridyl)-6-fluoro-7-chloro-1,4-dihydro-4-oxo-1,8-naphthyridine-3-carboxylic acid A procedure substantially similar to the procedure in Preparation 12 is carried out to prepare the title compound.

m.p.: 228°–230° C.

$^1$H NMR (CDCl$_3$, ppm): 8.50–8.74(m, 2H), 9.16–9.42(m, 3H)

Preparation 14

Preparation of 1-(5-fluoro-2-pyridyl)-6,7-difluoro-1,4-dihydro-4-oxoquinoline-3-carboxylic acid A procedure substantially similar to the procedure in Preparation 12 is carried out to prepare the title compound.

m.p.: 275°–280° C.

$^1$H NMR (CF$_3$COOD, ppm): 7.40(dd, 1H, J=3.02 Hz, J=10.06 Hz), 7.92–8.18(m, 2H), 8.39–8.78(m, 2H), 9.50(s, 1H)

Preparation 15

Preparation of 1-(5-fluoro-2-pyridyl)-6-fluoro-7-chloro-1,4-dihydro-4-oxo-1,8-naphthyridine-3-carboxylic acid A procedure substantially similar to the procedure in Preparation 12 is carried out to prepare the title compound.

m.p.: 234°–238° C.

$^1$H NMR (CDCl$_3$, ppm): 8.58–8.84(m, 2H), 9.18–9.42(m, 3H)

Preparation 16

Preparation of ethyl 1-(5-fluoro-2-pyridyl)-6-fluoro-7-(1-piperazinyl)-1,4-dihydro-4-oxo- 1,8-naphthyridine-3-carboxylate 0.5 g of ethyl 1-(5-fluoro-2-pyridyl)-6-fluoro-7-chloro-1,4-dihydro-4-oxo-1,8-naphthyridine-3-carboxylate and 0.35 g of piperazine are added to 45 ml of pyridine.

The mixture is stirred at 10° C. for 1 hour and then concentrated under a reduced pressure and subjected to a column chromatography (acetone/n-hexane=5/2) to obtain

Preparation 17

Preparation of ethyl 1-(5-fluoro-2-pyridyl)-6-fluoro-7-(4-methyl-1-piperazinyl)-1,4-dihydro-4-oxo-1,8-naphthyridine-3-carboxylate A procedure substantially similar to the procedure in Preparation 16 is carried out to prepare the title compound.

Yield: 85.0%

Preparation 18

Preparation of ethyl 1-(5-fluoro-2-pyridyl)-6-fluoro-7-(3-methyl-1-piperazinyl)-1,4-dihydro-4-oxo-1,8-naphthyridine-3-carboxylate A procedure substantially similar to the procedure in Preparation 16 is carried out to prepare the title compound.

Yield: 91.5%

Preparation 19

Preparation of ethyl 1-(5-fluoro-2-pyridyl)-6-fluoro-7-(3,5-dimethyl-1-piperazinyl)-1,4-dihydro-4-oxo-1,8-naphthyridine-3-carboxylate A procedure substantially similar to the procedure in Preparation 16 is carried out to prepare the title compound.

Yield: 84.1% m.p.: 165° C.

$^1$H NMR(CDCl$_3$, ppm): 0.94(s, 3H), 1.00(s, 3H), 1.35(t, 3H, J=6.40 Hz), 2,24– 3.06(m, 4H), 4.00–4.42(m, 4H), 7.44–8.24(m, 3H), 8.38–8.52(m, 1H), 8.76(s, 1H)

Preparation 20

Preparation of ethyl 1-(5-fluoro-2-pyridyl)-6-fluoro-7-(3-acetamido-1-pyrrolidinyl)-1,4-dihydro-4-oxo-1,8-naphthyridine-3-carboxylate A procedure substantially similar to the procedure in Preparation 16 is carried out to prepare the title compound.

Yield: 90.3% m.p.: 200°–202° C.

$^1$H NMR (CDCl$_3$, ppm): 1.30(t, 3H, J=6.40 Hz), 1.90–2.16(m, 5H), 3.40–3.94(m, 4H), 4.28(q, 2H, J=6.4 Hz), 4.76(m, 1H), 7.44–8.06(m, 3H), 8.32–8.46(m, 1H), 8.68(s, 1H)

Preparation 21

Preparation of ethyl 1-(5-fluoro-2-pyridyl)-6,8-difluoro-7-(1-piperazinyl)-1,4-dihydro-4-oxoquinoline-3-carboxylate A procedure substantially similar to the procedure in Preparation 16 is carried out to prepare the title compound.

Yield: 90.3%

Preparation 22

Preparation of ethyl 1-(5-fluoro-2-pyridyl)-6,8-difluoro-7-(4-methyl-1-piperazinyl)-1,4-dihydro-4-oxoquinoline-3-carboxylate A procedure substantially similar to the procedure in Preparation 16 is carried out to prepare the title compound.

Yield: 91.3%

Preparation 23

Preparation of ethyl 1-(5-fluoro-2-pyridyl)-6,8-difluoro-7-(3-methyl-1-piperazinyl)-1,4-dihydro-4-oxoquinoline-3-carboxylate A procedure substantially similar to the procedure in Preparation 16 is carried out to prepare the title compound.

Yield: 87.5%

Preparation 24

Preparation of ethyl 1-(5-fluoro-2-pyridyl)-6,8-difluoro-7-(3,5-dimethyl-1-piperazinyl)-1,4-dihydro-4-oxoquinoline-3-carboxylate A procedure substantially similar to the procedure in Preparation 16 is carried out to prepare the title compound.

Yield: 89.3%

Preparation 25

Preparation of ethyl 1-(5-fluoro-2-pyridyl)-6,8-difluoro-7-(3-acetamido-1-pyrrolidinyl)-1,4-dihydro-4-oxoquinoline-3-carboxylate A procedure substantially similar to the procedure in Preparation 16 is carried out to prepare the title compound.

Yield: 90.3%

Preparation 26

Preparation of ethyl 1-(5-fluoro-2-pyridyl)-6-fluoro-7-(1-piperazinyl)-1,4-dihydro-4-oxoquinoline-3-carboxylate A procedure substantially similar to the procedure in Preparation 16 is carried out to prepare the title compound.

Yield: 84.5%

Preparation 27

Preparation of ethyl 1-(5-fluoro-2-pyridyl)-6-fluoro-7-(4-methyl-1-piperazinyl)-1,4-dihydro-4-oxoquinoline-3-carboxylate A procedure substantially similar to the procedure in Preparation 16 is carried out to prepare the title compound.

Yield: 88.7%

Preparation 28

Preparation of ethyl 1-(5-fluoro-2-pyridyl)-6-fluoro-7-(3-methyl-1-piperazinyl)-1,4-dihydro-4-oxoquinoline-3-carboxylate A procedure substantially similar to the procedure in Preparation 16 is carried out to prepare the title compound.

Yield: 83.7%

Preparation 29

Preparation of ethyl 1-(5-fluoro-2-pyridyl)-6-fluoro-7-(3,5-dimethyl-1-piperazinyl)-1,4-dihydro-4-oxoquinoline-3-carboxylate A procedure substantially similar to the procedure in Preparation 16 is carried out to prepare the title compound.

Yield: 88.7%

Preparation 30

Preparation of ethyl 1-(5-fluoro-2-pyridyl)-6-fluoro-7-(3-acetamido-1-pyrrolidinyl)-1,4-dihydro-4-oxoquinoline-3-carboxylate A procedure substantially similar to the procedure in Preparation 16 is carried out to prepare the title compound.

Yield: 92.7%

Preparation 31

Preparation of 1-(3-fluoro-4-pyridyl)-6-fluoro-7-(3-acetamido-1-pyrrolidinyl)-1,4-dihydro-4-oxoquinoline-3-carboxylic acid 0.22 g of 1-(3-fluoro-4-pyridyl)-6,7-difluoro-1,4-dihydro-4-oxoquinoline-3carboxylic acid and 0.11 g of 3-acetamidopyrrolidine are added to 12 ml of pyridine, and added with 0.13 ml of 1,8-diazabicyclo[5.4.0]undec-7-ene. The mixture is stirred at room temperature for 24 hours, and then concentrated under a reduced pressure to remove the solvent completely. The residue is added with 20 ml of acetone and stirred at room temperature for 1 hour to obtain a product, which is then filtered and dried and used in the next reaction. (next reaction: Example 5)

Preparation 32

Preparation of ethyl 5-methyl-7-(4-methyl-1-piperazinyl)-1-(5-fluoro-2-pyridyl)-6 fluoro-1,4-dihydro-4-oxoquinoline-3-carboxylate A procedure substantially similar to the procedure in Preparation 16 is carried out to prepare the title compound.

Yield: 82.5%

Preparation 33

Preparation of ethyl 5-methyl-7-(3-methyl-1-piperazinyl)-1-(5-fluoro-2-pyridyl)-6-fluoro-1,4-dihydro-4-oxoquinoline-3-carboxylate A procedure substantially similar to the procedure in Preparation 16 is carried out to prepare the title compound.

Yield: 85.0%

EXAMPLE 1

Preparation of 1-(3-fluoro-4-pyridyl)-6-fluoro-7-(1-piperazinyl)-1,4-dihydro-4-oxoquinoline-3-carboxylic acid hydrochloride 0.66 g of 1-(3-fluoro-4-pyridyl)-6,7-difluoro-1,4-dihydro-4-oxoquinoline-3-carboxylic acid and 0.22 mg of piperazine are added to 30 ml of pyridine. The mixture is added with 0.39 ml of 1,8-diazabicyclo[5.4.0]undec-7-ene, stirred at room temperature for 24 hours and concentrated under a reduced pressure. The concentrate is subjected to a column chromatography (chloroform/methanol/ammonia water:15/12/1) to seperate the desired product, which is then concentrated under a reduced pressure. After then, the residue is added with 15 ml of ethanol, 10 ml of water and 5 ml of conc. hydrochloric acid and stirred at room temperature for 3 hours, filtered and dried. The obtained product is recrystallized in a mixed solvent of methanol or ethanol and water to obtain 0.47 g of the desired compound.

m.p.: 284°–286° C. (dec.)

$^1$H NMR (CF$_3$COOD, ppm): 3.26–4.24(m, 8H), 6.84(d, 1H, J=4.82 Hz), 8.38(d, 1H, J=12.82 Hz), 8.70–9.02(m, 1H), 9.20–9.62(m, 3H)

EXAMPLE 2

Preparation of 1-(3-fluoro-4-pyridyl)-6-fluoro-7-(4-methyl-1-piperazinyl)-1,4-dihydro-4-oxoquinoline-3-carboxylic acid hydrochloride A procedure substantially similar to the procedure in Example 1 is carried out to prepare the title compound.

m.p.: 274°–276° C. (dec.)

$^1$H NMR (CF$_3$COOD, ppm): 3.12(s, 3H), 3.28–4.32(m, 8H), 6.88(d, 1H, J=4.80 Hz), 8.38(d, 1H, J=12.80 Hz), 8.68–8.98(m, 1H), 9.20–9.60(m, 3H)

EXAMPLE 3

Preparation of 1-(3-fluoro-4-pyridyl)-6-fluoro-7-(3-methyl-1-piperazinyl)-1,4-dihydro-4-oxoquinoline-3-carboxylic acid hydrochloride A procedure substantially similar to the procedure in Example 1 is carried out to prepare the title compound.

m.p.: 270°–272° C. (dec.)

$^1$H NMR (CF$_3$COOD, ppm): 1.52(d, 3H, J=5.62 Hz), 3.36–4.24(m, 7H), 6.86(d, 1H, J=4.80 Hz), 8.36(d, 1H, J=12.80 Hz), 8.70–8.92(m, 1H), 9.26–9.60(m, 3H)

EXAMPLE 4

Preparation of 1-(3-fluoro-4-pyridyl)-6-fluoro-7-(3,5-dimethyl-1-piperazinyl)-1,4 dihydro-4-oxoquinoline-3-carboxylic acid hydrochloride A procedure substantially similar to the procedure in Example 1 is carried out to prepare the title compound.

m.p.: 285°–287° C. (dec.)

$^1$H NMR (CF$_3$COOD, ppm): 1.38–1.62(m, 6H), 3.20–4.28(m, 6H), 6.90(d, 1H, J=4.80 Hz), 8.38(d, 1H, J=12.80 Hz), 8.68–9.00(m, 1H), 9.20–9.56(m, 3H)

EXAMPLE 5

Preparation of 1-(3-fluoro-4-pyridyl)-6-fluoro-7-(3-amino-1-pyrrolidinyl)-1,4-dihydro-4-oxoquinoline-3-carboxylic acid hydrochloride 0.5 g of 1-(3-fluoro-4-pyridyl)-6-fluoro-7-(3-acetamido-1-pyrrolidyl)-1,4-dihydro-4-oxoquinoline-3-carboxylic acid is added to 15 ml of ethanol, 10 ml of water and 5 ml of conc. hydrochloric acid. The reaction mixture is refluxed for 18 hours, cooled and concentrated under a reduced pressure to remove the solvent completely.

The residue is recrystallized in a mixed solvent of ethanol and water to obtain 0.22 g of the desired compound.

m.p.: 274°–276° C. (dec.)

$^1$H NMR (CF$_3$COOD, ppm): 2.38–2.70(m,2H), 3.60–4.08(m, 2H), 4.10–4.52(m, 3H), 6.24(d, 1H, J=4.80 Hz), 8.22(d, 1H, J=12.82 Hz), 8.68–9.00(m, 1H), 9.16–9.60(m, 3H)

EXAMPLE 6

Preparation of 1-(3-fluoro-4-pyridyl)-6-fluoro-7-[(3S)-3-amino-1-pyrrolidinyl]-1,4-dihydro-4-oxoquinoline-3-carboxylic acid A procedure substantially similar to the procedure in Example 1 is carried out to prepare the title compound.

m.p.: 225°–227° C. (dec.)

$^1$H NMR(CF$_3$COOD, ppm): 2.38–2.72(m, 2H), 3.60–3.98(m, 2H), 4.18–4.60(m, 3H), 6.26(d, 1H, J=4.80 Hz), 8.28(d, 1H, J=12.82 Hz), 8.58–8.84(m, 1H), 9.12–9.52(m, 3H)

EXAMPLE 7

Preparation of 1-(3-fluoro-4-pyridyl)-6-fluoro-7-(1-piperazinyl)-1,4-dihydro-4-oxo- 1,8-naphthyridine-3-carboxylic acid hydrochloride A procedure substantially similar to the procedure in Example 1 is carried out to prepare the title compound.

m.p.: 273°–275° C. (dec.)

$^1$H NMR(CF$_3$COOD, ppm): 3.42–4.60(m, 8H), 8.32(d, 1H, J=12.02 Hz), 8.60–8.86(m, 1H), 9.10–9.58(m, 3H)

EXAMPLE 8

Preparation of 1-(3-fluoro-4-pyridyl)-6-fluoro-7-(4-methyl-1-piperazinyl)-1,4-dihydro- 4-oxo-1,8-naphthyridine-3-carboxylic acid hydrochloride A procedure substantially similar to the procedure in Example 1 is carried out to prepare the title compound.

m.p.: 275° C.

$^1$H NMR(CF$_3$COOD, ppm): 3.10(s, 3H), 3.14–4.10(m, 6H), 4.26–4.92(m, 2H), 8.30(d, 1H, J=12.00 Hz), 8.60–8.88(m, 1H), 9.20–9.50(m, 3H)

EXAMPLE 9

Preparation of 1-(3-fluoro-4-pyridyl)-6-fluoro-7-(3-methyl-1-piperazinyl)-1,4-dihydro- 4-oxo-1,8-naphthyridine-3-carboxylic acid hydrochloride A procedure substantially similar to the procedure in Example 1 is carried out to prepare the title compound.

m.p.: 277°–279° C. (dec.)

$^1$H NMR(CF$_3$COOD, ppm): 1.32–1.68(m, 3H), 3.32–4.08(m, 5H), 4.34–4.84(m, 2H), 8.32(d, 1H, J=12.02 Hz), 8.60–8.90(m, 1H), 9.20–9.50(m, 3H)

EXAMPLE 10

Preparation of 1-(3-fluoro-4-pyridyl)-6-fluoro-7-(3,5-dimethyl-1-piperazinyl)-1,4 -dihydro-4-oxo-1,8-naphthyridine-3-carboxylic acid hydrochloride A procedure substantially similar to the procedure in Example 1 is carried out to prepare the title compound.

m.p.: 270° C. (dec.)

$^1$H NMR(CF$_3$COOD, ppm): 1.30–1.60(m, 6H), 3.32–3.92(m, 4H), 4.44–4.92(m, 2H), 8.36(d, 1H, J=12.02 Hz), 8.62–8.90(m, 1H), 9.16–9.52(m, 3H)

EXAMPLE 11

Preparation of 1-(3-fluoro-4-pyridyl)-6-fluoro-7-[(3S)-3-amino-1-pyrrolidinyl]-1,4 -dihydro-4-oxo-1,8-naphthyridine-3-carboxylic acid hydrochloride A procedure substantially similar to the procedure in Example 1 is carried out to prepare the title compound.

m.p.: 269° C.

$^1$H NMR(CF$_3$COOD, ppm): 2.14–2.84(m, 2H), 3.56–4.64(m, 5H), 8.23(d, 1H, J= 12.04 Hz), 8.62–8.96(m, 1H), 9.10–9.52(m, 3H)

EXAMPLE 12

Preparation of 1-(5-fluoro-2-pyridyl)-6-fluoro-7-(1-piperazinyl)-1,4-dihydro-4-oxo-1,8 -naphthyridine-3-carboxylic acid hydrochloride 0.5 g of ethyl 1-(5-fluoro-2-pyridyl)-6-fluoro-7-(1-piperazinyl)-1,4-dihydro-4-oxo- 1,8-naphthyridine-3-carboxylate is added to 10 ml of water and 10 ml of conc. hydrochloric acid. The mixture is refluxed for 24 hours, cooled to room temperature and concentrated under a reduced pressure. The concentrate is added with 20 ml of ethanol and stirred at room temperature for 2 hours, filtered and dried. The product is recrystallized in a mixed solvent of water and methanol to obtain 0.39 g of the desired compound.

m.p.: >300° C.

$^1$H NMR(CF$_3$COOD, ppm): 3.60–3.80(m, 4H), 4.14–4.46(m, 4H), 7.92–8.50(m, 3H), 8.70(bs, 1H), 9.40(s, 1H)

EXAMPLE 13

Preparation of 1-(5-fluoro-2-pyridyl)-6-fluoro-7-(4-methyl-1-piperazinyl)-1,4-dihydro- 4-oxo-1,8-naphthyridine-3-carboxylic acid hydrochloride A procedure substantially similar to the procedure in Example 12 is carried out to prepare the title compound.

m.p.: 275°–277° C.

$^1$H NMR(CF$_3$COOD, ppm): 3.10(s, 3H), 3.60–5.00(m, 8H), 7.84–8.50(m, 3H), 8.68 (bs, 1H), 9.38(s, 1)

EXAMPLE 14

Preparation of 1-(5-fluoro-2-pyridyl)-6-fluoro-7-(3-methyl-1-piperazinyl)-1,4-dihydro- 4-oxo-1,8-naphthyridine-3-carboxylic acid hydrochloride A procedure substantially similar to the procedure in Example 12 is carried out to prepare the title compound.

m.p.: 268° C. (dec.)

$^1$H NMR(CF$_3$COOD, ppm): 1.40–1.80(m, 3H), 3.50–3.90(m, 5H), 4.58–4.80(m, 2H), 8.12–8.48(m, 3H), 8.74(bs, 1H), 9.40(s, 1H)

EXAMPLE 15

Preparation of 1-(5-fluoro-2-pyridyl)-6-fluoro-7-(3,5-dimethyl-1-piperazinyl)-1,4 -dihydro-4-oxo-1,8-naphthyridine-3-carboxylic acid hydrochloride A procedure substantially similar to the procedure in Example 12 is carried out to prepare the title compound.

m.p.: 289° C. (dec.)

$^1$H NMR(CF$_3$COOD, ppm): 1.30–1.64(m, 6H), 3.28–4.00(m, 4H), 4.52–4.92(m, 2H), 7.96–8.48(m, 3H), 8.78(bs, 1H), 9.40(s, 1H)

EXAMPLE 16

Preparation of 1-(5-fluoro-2-pyridyl)-6-fluoro-7-(3-amino-1-pyrrolidinyl)-1,4-dihydro- 4-oxo-1,8-naphthyridine-3-carboxylic acid hydrochloride 0.5 g of ethyl 1-(5-fluoro-2-pyridyl)-6-fluoro-7-(acetamido-1-pyrrolidinyl)-1,4 -dihydro-4-oxo-1,8-naphthyridine-3-carboxylate is added to 10 ml of water and 10 ml of conc. hydrochloric acid. The mixture is refluxed for 24 hours, cooled to room temperature and concentrated under a reduced pressure. The concentrate is added with 20 ml of ethanol and dissolved completely. After then, 70 ml of ethyl ether is added for precipitation, and then stirred at room temperature for 2 hours, filtered and dried. The product is recrystallized in a mixed solvent of methanol and water to obtain 0.35 g of the desired compound m.p.: 208°–210° C.

$^1$H NMR(CF$_3$COOD, ppm): 2.30–2.80(m, 2H), 3.78–4.68(m, 5H), 7.96–8.32(m, 3H), 8.70(bs, 1H), 9.32(s, 1H)

EXAMPLE 17

Preparation of 1-(5-fluoro-2-pyridyl)-6-fluoro-7-(1-piperazinyl)-1,4-dihydro-4 -oxoquinoline-3-carboxylic acid hydrochloride A procedure substantially similar to the procedure in Example 12 is carried out to prepare the title compound.

m.p.: 300° C. (dec.)

$^1$H NMR(CF$_3$COOD, ppm): 3.51–4.05(m, 8H), 6.80(d, 1H,J=7.60 Hz), 7.84–8.21(m, 2H), 8.32(d, 1H, J=12.04 Hz), 8.70(bs, 1H), 9.30(s, 1H)

EXAMPLE 18

Preparation of 1-(5-fluoro-2-pyridyl)-6-fluoro-7-(4-methyl-1-piperazinyl)-1,4-dihydro- 4-oxoquinoline-3-carboxylic acid hydrochloride A procedure substantially similar to the procedure in Example 12 is carried out to prepare the title compound.

m.p.: >300° C. (dec.)

$^1$H NMR(CF$_3$COOD, ppm): 3.12(s, 3H), 3.28–4.29(m, 5H), 6.81(d, 1H, J=7.60 Hz), 7.84–8.15(m, 2H), 8.33(d, 1H, J=12.20 Hz), 8.71 (bs, 1H), 9.29(s, 1H)

EXAMPLE 19

Preparation of 1-(5-fluoro-2-pyridyl)-6-fluoro-7-(3-methyl-1-piperazinyl)-1,4-dihydro- 4-oxoquinoline-3-carboxylic acid hydrochloride A procedure substantially similar to the procedure in Example 12 is carried out to prepare the title compound.

m.p.: 295° C. (dec.)

$^1$H NMR(CF$_3$COOD, ppm): 1.51(d, 3H, J=4.40 Hz), 3.23–4.11(m, 7H), 6.80(d, 1H, J=6.20 Hz), 7.96–8.16(m, 2H), 8.30(d, 1H, J=14.00 Hz), 8.69(s, 1H), 9.30(s, 1H)

EXAMPLE 20

Preparation of 1-(5-fluoro-2-pyridyl)-6-fluoro-7-(3,5-dimethyl-1-piperazinyl)-1,4 -dihydro-4-oxoquinoline-3-carboxylic acid hydrochloride A procedure substantially similar to the procedure in Example 12 is carried out to prepare the title compound.

m.p.: 297° C. (dec.)

$^1$H NMR(CF$_3$COOD, ppm): 1.30–1.65(m, 6H), 3.10–4.57(m, 6H), 6.89(d, 1H, J=6.20 Hz), 7.93–8.20(m, 2H), 8.70(d, 1H, J=12.82 Hz), 8.48(s, 1H), 9.32(s, 1H)

EXAMPLE 21

Preparation of 1-(5-fluoro-2-pyridyl)-6-fluoro-7-(3-amino-1-pyrrolidinyl)-1,4-dihydro- 4-oxoquinoline-3-carboxylic acid hydrochloride A procedure substantially similar to the procedure in Example 16 is carried out to prepare the title compound.

m.p.: 275° C. (dec.)

$^1$H NMR(CF$_3$COOD, ppm): 2.40–2.73(m, 2H), 3.60–4.56(m, 5H), 6.33(d, 1H, J=6.20 Hz), 7.98–8.37(m, 3H), 8.75(s, 1H), 9.24(s, 1H)

EXAMPLE 22

Preparation of 1-(5-fluoro-2-pyridyl)-6-fluoro-7-[(3S)-3-amino-1-pyrrolidinyl]-1,4 -dihydro-4-oxoquinoline-3-carboxylic acid hydrochloride A procedure substantially similar to the procedure in Example 1 is carried out to prepare the title compound.

m.p.: 268°–272° C. (dec.)

$^1$H NMR(CF$_3$COOD, ppm): 2.40–2.73(m, 2H), 3.60–4.56(m, 5H), 6.33(d, 1H, J= 6.20 Hz), 7.98–8.37(m, 3H), 8.75(s, 1H), 9.24(s, 1H)

EXAMPLE 23

Preparation of 1-(5-fluoro-2-pyridyl)-6,8-difluoro-7-(1-piperazinyl)-1,4-dihydro-4 -oxoquinoline-3-carboxylic acid hydrochloride A procedure substantially similar to the procedure in Example 12 is carried out to prepare the title compound.

m.p.: 300° C. (dec.)

$^1$H NMR(CF$_3$COOD, ppm): 3.76–4.02(m, 5H), 8.00–8.48(m, 3H), 8.68(bs, 1H), 9.32 (s, 1H)

EXAMPLE 24

Preparation of 1-(5-fluoro-2-pyridyl)-6,8-difluoro-7-(4-methyl-1-piperazinyl)-1,4 -dihydro-4-oxoquinoline-3-carboxylic acid hydrochloride A procedure substantially similar to the procedure in Example 12 is carried out to prepare the title compound.

m.p.: 247° C. (dec.)

$^1$H NMR(CF$_3$COOD, ppm): 3.10(s, 3H), 3.20–4.00(m, 5H), 7.98–8.38(m, 3H), 8.58 (bs, 1H), 9.30(s, 1H)

EXAMPLE 25

Preparation of 1-(5-fluoro-2-pyridyl)-6,8-difluoro-7-(3-methyl-1-piperazinyl)-1,4 -dihydro-4-oxoquinoline-3-carboxylic acid hydrochloride A procedure substantially similar to the procedure in Example 12 is carried out to prepare the title compound.

m.p.: 295° C. (dec.)

$^1$H NMR(CF$_3$COOD, ppm): 1.45–1.60(d, 3H, J=3.20 Hz), 3.38–4.02(m, 7H), 7.92– 8.50(m, 3H), 8.70(bs, 1H), 9.30(s, 1H)

EXAMPLE 26

Preparation of 1-(5-fluoro-2-pyridyl)-6,8-difluoro-7-(3,5-dimethyl-1-piperazinyl)-1,4 -dihydro-4-oxoquinoline-3-carboxylic acid hydrochloride A procedure substantially similar to the procedure in Example 12 is carried out to prepare the title compound.

m.p.: 297° C. (dec.)

$^1$H NMR(CF$_3$COOD, ppm): 1.32–1.60(m, 6H), 3.38–3.90(m, 6H), 7.96–8.41(m, 3H), 8.64(bs, 1H), 9.32(s, 1H)

EXAMPLE 27

Preparation of 1-(5-fluoro-2-pyridyl)-6,8-difluoro-7-(3-amino-1-pyrrolidinyl)-1,4 -dihydro-4-oxoquinoline-3-carboxylic acid hydrochloride A procedure substantially similar to the procedure in Example 16 is carried out to prepare the title compound.

m.p.: 275° C. (dec.)

$^1$H NMR(CF$_3$COOD, ppm): 2.40–2.60(m, 2H), 3.98–4.24(m, 5H), 8.08–8.38(m, 3H), 8.64(s, 1H), 9.24(s, 1H)

EXAMPLE 28

Preparation of 5-methyl-7-(4-methyl-1-piperazinyl)-1-(5-fluoro-2-pyridyl)-6-fluoro- 1,4-dihydro-4-oxoquinoline-3-carboxylic acid hydrochloride A procedure substantially similar to the procedure in Example 12 is carried out to prepare the title compound.

m.p.: 262° C. (dec.)
$^1$H NMR(CF$_3$COOD, ppm): 2.99(s, 3H), 3.10(s, 3H), 3.15–4.20(m, 8H), 6.60(d, 1H, J=7.20 Hz), 8.02(m, 2H), 8.70(s, 1H), 9.24(s, 1H)

EXAMPLE 29

Preparation of 5-methyl-7-(3-methyl-1-piperazinyl)-1-(5-fluoro-2-pyridyl)-6-fluoro- 1,4-dihydro-4-oxoquinoline-3-carboxylic acid hydrochloride A procedure substantially similar to the procedure in Example 12 is carried out to prepare the title compound.

m.p.: 276° C. (dec.)
$^1$H NMR(CF$_3$COOD, ppm): 1.60(d, 3H, J=6.00 Hz), 2.97(s, 3H), 3.15–4.21(m, 7H), 6.60(d, 1H, J=8.00 Hz), 8.40(m, 2H), 8.65(s, 1H), 9.25(s, 1H)

The in vitro antibiotic activity of the present compound is measured using 2-fold dilution method with a micro-well plate and the bacteria are inoculated in about 10$^5$ cfu/ml after an overnight culture in a brain-heart infusion (BHI) broth at 37° C. The novel compounds of the present invention are converted to a hydrochloride salt form and diluted with a sterilized distilled water to make 10 mg/ml aqueous solution. After the mother liquor wherein the compound is diluted to the two-fold concentration has been obtained in the form of an aqueous solution, the respective 0.1 ml of diluted liquor is transferred to a well and is inoculated with 0.1 ml of the culture fluid to make about (10$^5$–10$^6$)/2 cfu/ml.

After cultivation at 37° C., the minimum inhibitory concentration (MIC) is measured and recorded in Table I–V.

Table I–V show the minimum inhibitory concentrations (MIC).

TABLE I

Minimum Inhibitory Concentration (μg/ml)

| Strains | Example 1 | 2 | 3 | 4 | 5 | 6 |
|---|---|---|---|---|---|---|
| A. calcoaceticus ATCC8090 | 0.625 | 0.625 | 0.625 | 2.50 | 0.313 | 0.156 |
| C. freundii ATCC8090 | 1.25 | 0.625 | 1.25 | 1.25 | 0.313 | 0.313 |
| E. aerogenes ATCC13048 | 1.25 | 1.25 | 1.25 | 1.25 | 0.156 | 0.313 |
| E. cloacae ATCC13048 | 0.625 | 0.625 | 0.625 | 0.625 | 0.313 | 0.156 |
| E. coli ATCC25922 | 1.25 | 1.25 | 0.625 | 1.25 | 0.156 | 0.078 |
| H. influenzae ATCC35056 | 0.625 | 0.625 | 1.25 | 1.25 | 0.313 | 0.313 |
| K. pneumoniae ATCC13883 | 0.625 | 0.625 | 0.625 | 0.625 | 0.156 | 0.156 |
| P. vulgaris ATCC13315 | 0.625 | 0.625 | 0.625 | 0.625 | 0.078 | 0.078 |
| P. aerugirnosa ATCC27853 | 0.625 | 0.625 | 0.625 | 0.625 | 0.313 | 0.156 |
| S. typhisurium ATCC14028 | 0.625 | 0.625 | 0.625 | 1.25 | 0.313 | 0.156 |
| S. flexneri ATCC12022 | 0.625 | 0.625 | 2.50 | 1.25 | 0.625 | 0.313 |
| S. sonnei ATCC25931 | 0.625 | 0.625 | 0.625 | 0.625 | 0.078 | 0.020 |
| S. marcescens ATCC8100 | 0.313 | 0.625 | 0.625 | 1.25 | 0.313 | 0.078 |
| S. faecalis ATCC19433 | 5 | 5 | 2.50 | 5 | 2.50 | 1.25 |
| S. faecalis ATCC29212 | 5 | 5 | 5 | 5 | 2.50 | 2.50 |
| S. pneuinoniae ATCC6303 | 2.50 | 10 | 5 | 10 | 2.50 | 2.50 |
| S. pyrogenes ATCC19615 | 5 | 10 | 10 | 10 | 5 | 2.50 |

TABLE II

Minimum Inhibitory Concentration (μg/ml)

| Strains | Example 7 | 8 | 9 | 10 | 11 | 12 |
|---|---|---|---|---|---|---|
| A. calcoaceticus ATCC8090 | 2.50 | 1.25 | 10 | 10 | 1.25 | 0.625 |
| C. freundii ATCC8090 | 1.25 | 1.25 | 1.25 | 1.25 | 0.156 | 1.25 |
| E. aerogenes ATCC13048 | 0.625 | 0.625 | 0.625 | 1.25 | 0.156 | 0.625 |
| E. cloacae ATCC13048 | 0.625 | 0.625 | 0.625 | 0.625 | 0.156 | 0.625 |
| E. coli ATCC25922 | 0.625 | 0.313 | 0.625 | 1.25 | 0.078 | 0.313 |
| H. influenzae ATCC35056 | 0.313 | 0.625 | 1.25 | 0.625 | 0.156 | 1.25 |
| K. pneumoniae ATCC13883 | 0.625 | 0.625 | 1.255 | 0.625 | 0.156 | 0.625 |
| P. vulgaris ATCC13315 | 0.313 | 0.313 | 0.625 | 0.625 | 0.313 | 0.625 |
| P. aerugirnosa ATCC27853 | 0.625 | 0.625 | 0.625 | 0.25 | 0.156 | 1.25 |
| S. typhisurium ATCC14028 | 0.313 | 0.313 | 0.625 | 0.625 | 0.156 | 1.25 |
| S. flexneri ATCC12022 | 0.156 | 0.313 | 0.625 | 0.625 | 0.156 | 0.625 |
| S. sonnei ATCC25931 | 0.313 | 0.625 | 0.625 | 0.625 | 0.010 | 0.313 |
| S. marcescens ATCC8100 | 1.25 | 0.625 | 1.25 | 2.50 | 0.156 | 1.25 |
| S. faecalis ATCC19433 | 2.50 | 5 | 2.50 | 2.50 | 0.625 | 5 |
| S. faecalis ATCC29212 | 5 | 5 | 2.50 | 5 | 0.625 | 5 |
| S. pneuinoniae ATCC6303 | 2.50 | 5 | 5 | 5 | 1.25 | 5 |
| S. pyrogenes ATCC19615 | 5 | 10 | 10 | 10 | 2.50 | 5 |

TABLE IV

Minimum Inhibitory Concentration (μg/ml)

| Strains | Example 13 | 14 | 15 | 16 | 17 | 18 |
|---|---|---|---|---|---|---|
| A. calcoaceticus ATCC8090 | 0.313 | 0.625 | 0.625 | 0.156 | 2.50 | 0.625 |
| C. freundii ATCC8090 | 0.156 | 0.625 | 0.313 | 0.078 | 1.25 | 0.625 |
| E. aerogenes ATCC13048 | 0.625 | 1.25 | 1.25 | 0.313 | 1.25 | 0.25 |
| E. cloacae ATCC13048 | 0.313 | 0.625 | 0.625 | 0.156 | 1.25 | 0.625 |
| E. coli ATCC25922 | 0.156 | 0.313 | 0.625 | 0.078 | 0.313 | 0.625 |
| H. influenzae ATCC35056 | 0.625 | 1.25 | 2.50 | 0.078 | 1.25 | 0.625 |
| K. pneumoniae ATCC13883 | 0.625 | 1.25 | 0.625 | 0.078 | 0.625 | 0.625 |
| P. vulgaris ATCC13315 | 0.625 | 0.625 | 1.25 | 0.078 | 0.625 | 0.313 |
| P. aerugirnosa | 1.25 | 1.25 | 1.25 | 0.156 | 1.25 | 1.25 |

TABLE IV-continued

Minimum Inhibitory Concentration (μg/ml)

| Strains | Example 13 | 14 | 15 | 16 | 17 | 18 |
|---|---|---|---|---|---|---|
| ATCC27853 | | | | | | |
| S. typhisurium ATCC14028 | 0.313 | 1.25 | 1.25 | 0.313 | 1.25 | 1.25 |
| S. flexneri ATCC12022 | 0.156 | 0.156 | 0.313 | 0.039 | 0.625 | 0.625 |
| S. sonnei ATCC25931 | 0.156 | 0.078 | 0.078 | 0.020 | 0.625 | 0.625 |
| S. marcescens ATCC8100 | 0.313 | 0.313 | 1.25 | 0.078 | 2.50 | 1.25 |
| S. faecalis ATCC19433 | 5 | 5 | 5 | 1.25 | 5 | 5 |
| S. faecalis ATCC29212 | 5 | 2.50 | 5 | 0.625 | 2.50 | 2.50 |
| S. pneuinoniae ATCC6303 | 2.50 | 5 | 10 | 1.25 | 5 | 5 |
| S. pyrogenes ATCC19615 | 5 | 10 | 10 | 2.50 | 5 | 5 |

TABLE IV

Minimum Inhibitory Concentration (μg/ml)

| Strain | Example 19 | 20 | 21 | 22 | 23 | 24 |
|---|---|---|---|---|---|---|
| A. calcoaceticus ATCC8090 | 1.25 | 1.25 | 0.156 | 0.313 | 1.25 | 0.625 |
| C. freundii ATCC8090 | 1.25 | 0.625 | 0.078 | 0.039 | 0.625 | 0.625 |
| E. aerogenes ATCC13048 | 0.625 | 1.25 | 0.156 | 0.078 | 0.625 | 0.625 |
| E. cloacae ATCC13048 | 0.625 | 0.625 | 0.156 | 0.078 | 0.625 | 0.625 |
| E. coli ATCC25922 | 0.078 | 0.625 | 0.078 | 0.039 | 0.625 | 0.625 |
| H. influenzae ATCC35056 | 0.625 | 1.25 | 0.078 | 0.078 | 0.625 | 0.313 |
| K. pneumoniae ATCC13883 | 1.25 | 0.625 | 0.078 | 0.039 | 1.25 | 0.625 |
| P. vulgaris ATCC13315 | 0.156 | 0.625 | 0.078 | 0.078 | 0.313 | 0.625 |
| P. aeruginosa ATCC27853 | 0.625 | 1.25 | 0.313 | 0.156 | 1.25 | 0.625 |
| S. typhisurium ATCC14028 | 0.313 | 1.25 | 0.156 | 0.078 | 0.313 | 0.313 |
| S. flexneri ATCC12022 | 0.313 | 0.625 | 0.078 | 0.156 | 0.313 | 0.625 |
| S. sonnei ATCC25931 | 0.313 | 0.313 | 0.020 | 0.039 | 0.078 | 0.156 |
| S. marcescens ATCC8100 | 0.625 | 0.625 | 0.078 | 0.078 | 0.625 | 0.625 |
| S. faecalis ATCC19433 | 5 | 5 | 1.25 | 0.625 | 5 | 5 |
| S. faecalis ATCC29212 | 5 | 2.50 | 1.25 | 1.25 | 5 | 2.50 |
| S. pneuinoniae ATCC6303 | 5 | 5 | 2.50 | 1.25 | 2.50 | 5 |
| S. pyrogenes ATCC19615 | 10 | 10 | 2.50 | 2.50 | 5 | 10 |

TABLE V

Minimu Inhibitory Concentration (μg/ml)

| Strain | Example 25 | 26 | 27 | 28 | 29 |
|---|---|---|---|---|---|
| A. calcoaceticus ATCC8090 | 1.25 | 1.25 | 0.313 | 1.25 | 0.625 |
| C. freundii ATCC8090 | 0.625 | 1.25 | 0.156 | 2.50 | 0.625 |
| E. aerogenes ATCC13048 | 0.625 | 0.625 | 0.156 | 0.625 | 0.313 |
| E. cloacae ATCC13048 | 0.625 | 1.25 | 0.313 | 0.625 | 0.313 |
| E. coli ATCC25922 | 0.625 | 0.625 | 0.078 | 1.25 | 1.25 |
| H. influenzae ATCC35056 | 0.625 | 1.25 | 0.078 | 0.313 | 0.625 |
| K. pneumoniae ATCC13883 | 0.625 | 0.625 | 0.156 | 1.25 | 1.25 |
| P. vulgaris ATCC13315 | 0.625 | 0.255 | 0.156 | 0.625 | 1.25 |
| P. aeruginosa ATCC27853 | 0.313 | 0.625 | 0.313 | 1.25 | 1.25 |
| S. typhisurium ATCC14028 | 0.625 | 0.625 | 0.078 | 1.25 | 0.625 |
| S. flexneri ATCC12022 | 0.156 | 0.313 | 0.078 | 0.625 | 0.625 |
| S. sonnei ATCC25931 | 0.156 | 0.313 | 0.005 | 1.25 | 0.625 |
| S. marcescens ATCC8100 | 1.25 | 1.25 | 0.313 | 1.25 | 1.25 |
| S. faecalis ATCC19433 | 5 | 5 | 1.25 | 10 | 5 |
| S. faecalis ATCC29212 | 5 | 5 | 2.50 | 5 | 5 |
| S. pneuinoniae ATCC6303 | 5 | 5 | 2.50 | 10 | 10 |
| S. pyrogenes ATCC19615 | 10 | 10 | 2.50 | 10 | 10 |

The following are the original names for strains in Table I–V.

Acinetobacter calcoaceticus ATCC 19606

Citrobacter freundii ATCC 8090

Enterobacter aerogenes ATCC 13048

Enterobacter cloacae ATCC 23355

Escherichia coli ATCC 25922

Haemophilus influenza ATCC 35056

Klebsiella pneumoniae ATCC 13883

Proteus vulgaris ATCC 13315

Pseudomonas aeruginosa ATCC 27853

Salmonella typhimurium ATCC 14028

Shigella flexneri ATCC 12022

Shigella sonnei ATCC 25931

Serratia marcescens ATCC 8100

Streptococcus faecalis ATCC 19433

Streptococcus faecalis ATCC 29212

Streptococcus pneumoniae ATCC 6303

Streptococcus pyrogens ATCC 19615

The pharmacokinetic properties are tested by orally administrating and subcutaneously injecting a test compound and a substance for control to a ICR Mouse with 22 g±10% weight, drawing blood after 10, 20, 30, 45, 60, 90, 120, 150, 180 and minutes and analyzed by Bio-Assay (Agar well method).

The average values from four tests for each compound are recorded in the following Table VI.

TABLE VI

| Example | Route | Dose (mg/kg) | $t_{1/2}$ (h) | $C_{max}$ (μg/ml) | $T_{max}$ (h) | AUC (μg·h/ml) | Bioavail- ability (%) | Urine Recovery (%) |
|---|---|---|---|---|---|---|---|---|
| 13 | P.O | 40 | 8.07 | 11.46 | 1.12 | 41.05 | 73.95 | 19.59 |
|  | S.C | 40 | 11.46 | 8.00 | 0.81 | 55.51 |  | 30.82 |
| 14 | P.O | 40 | 3.81 | 2.12 | 0.87 | 12.46 | 44.00 | 58.89 |
|  | S.C | 40 | 7.28 | 4.28 | 0.60 | 28.07 |  | 21.10 |
| 18 | P.O | 40 | 3.44 | 9.18 | 0.94 | 42.24 | 68.56 | 28.14 |
|  | S.C | 40 | 3.15 | 19.56 | 1.00 | 63.45 |  | 39.85 |
| 19 | P.O | 40 | 8.42 | 3.11 | 0.87 | 16.92 | 72.74 | 29.00 |
|  | S.C | 40 | 5.32 | 5.11 | 0.87 | 23.26 |  | 48.69 |
| 28 | P.O | 40 | 7.57 | 6.36 | 0.87 | 62.44 | 81.28 | 25.24 |
|  | S.C | 40 | 7.26 | 6.94 | 1.00 | 76.12 |  | 13.36 |
| 29 | P.O | 40 | N.D | N.D | N.D | N.D | N.D. | 9.35 |
|  | S.C | 40 | 2.31 | 8.34 | 1.25 | 32.59 |  | 12.80 |
| Ciproflo-xacin | P.O | 40 | 0.92 | 1.71 | 1.47 | 2.27 | 14.60 | 21.10 |
|  | S.C | 40 | 2.37 | 7.77 | 1.56 | 15.55 |  | 61.80 |
| Ofloxacin | P.O | 40 | N.D | 9.41 | 0.75 | 12.79 | 89.75 | 32.20 |
|  | S.C | 40 | 0.42 | 12.93 | 0.42 | 14.25 |  | 39.10 |

The $LD_{50}$ of example 13 was about 1,000 g/kg and example 18 about >3,000 g/kg. (Oral, mice)

What is claimed is:

1. The quinolone carboxylic acid derivative 1-(5-fluoro-2-pyridyl)-6-fluoro-7-(4-methyl-1-piperazinyl)-1,4-dihydro-4-oxo-1,8-naphthyridine-3-carboxylic acid, or a pharmaceutically acceptable salt or hydrate thereof.

2. The quinolone carboxylic acid derivative 1-(5-fluoro-2-pyridyl)-6-fluoro-7-(4-methyl-1-piperazinyl)-1,4-dihydro-4-oxoquinoline-3-carboxylic acid, or a pharmaceutically acceptable salt or hydrate thereof.

* * * * *

UNITED STATES PATENT AND TRADEMARK OFFICE
CERTIFICATE OF CORRECTION

PATENT NO. : 5,496,947
DATED : March 5, 1996
INVENTOR(S) : Yoon et al.

It is certified that error appears in the above-indentified patent and that said Letters Patent is hereby corrected as shown below:

On title page, insert the foreign application priority information as follows:

-- [30]    Foreign Application Priority Data

Aug. 13, 1993  [KR]  Korea ............ 93-15724 --.

Signed and Sealed this

Twenty-third Day of July, 1996

Attest:

BRUCE LEHMAN

*Attesting Officer*    *Commissioner of Patents and Trademarks*